United States Patent
Ishimaru et al.

(10) Patent No.: US 7,468,265 B2
(45) Date of Patent: Dec. 23, 2008

(54) STABILIZING AGENT FOR ENZYMES

(75) Inventors: Takeshi Ishimaru, Tokyo (JP); Shuichi Miyaura, Kanagawa (JP)

(73) Assignee: Seikagaku Corporation, Tokyo (JP)

( * ) Notice: Subject to any disclaimer, the term of this patent is extended or adjusted under 35 U.S.C. 154(b) by 188 days.

(21) Appl. No.: 10/922,796

(22) Filed: Aug. 19, 2004

(65) Prior Publication Data

US 2005/0089934 A1 Apr. 28, 2005

(30) Foreign Application Priority Data

Aug. 20, 2003 (JP) ............................. 2003-296005
Mar. 26, 2004 (JP) ............................. 2004-093864
Mar. 29, 2004 (JP) ............................. 2004-096607
Jul. 2, 2004 (JP) ............................. 2004-197050

(51) Int. Cl.
*C12N 9/00* (2006.01)

(52) U.S. Cl. ....................................................... 435/183

(58) Field of Classification Search ........................ None
See application file for complete search history.

(56) References Cited

U.S. PATENT DOCUMENTS 3,575,864 A    4/1971   Innerfield
6,030,821 A *  2/2000   Soeda et al. ................. 435/188
6,117,433 A *  9/2000   Edens et al. ................. 424/400

FOREIGN PATENT DOCUMENTS

EP         0745 670  A1   12/1996

* cited by examiner

*Primary Examiner*—Michael V Meller
(74) *Attorney, Agent, or Firm*—Factor & Lake, Ltd.

(57) ABSTRACT

The present invention provides a safe and novel stabilizing agent for enzymes; a composition containing an enzyme and the stabilizing agent; and a kit containing the stabilizing agent composition. According to the invention, deactivation or inactivation of the activity of the enzyme during storage, drying, freezing, etc. can be prevented, without raising any problem of potential infection of an enzyme with a pathogen. For purposes of the invention, the stabilizing agent for an enzyme contains a plant-derived polypeptide as an active ingredient.

4 Claims, No Drawings

STABILIZING AGENT FOR ENZYMES

BACKGROUND OF THE INVENTION

1. Field of the Invention

The present invention relates to a stabilizing agent for enzymes, to a composition containing the agent, and to a kit or a similar product containing the agent.

2. Description of the Related Art

Generally, functions of enzymes are known to be related to a stereostructure thereof, and the functions are known to be lost or inactivated as a result of change in stereostructure during storage thereof. Since enzymes are generally supplied in the form of lyophilized products, a variety of studies have been carried out on methods for preventing deactivation or denaturation of enzymes during lyophilization. Among such methods, addition of an amino acid or protein such as sodium glutamate, albumin, or skim milk; addition of a sugar such as sucrose or maltose; addition of a reducing agent such as glutathione or mercaptoethanol; addition of a polyhydric alcohol such as glycerol or sorbitol, and a similar method are generally known.

Techniques for stabilizing enzymes through employment of a plant-derived protein or a degraded product thereof are also disclosed. For example, WO 96/11264 discloses a technique in which a hydrolyzate of protein derived from wheat, soybean, etc. is employed as a stabilizing agent for transglutaminase, which is an enzyme widely employed in food processing industry. However, the document neither discloses nor suggests stabilization of enzymes for use in analysis (hereinafter referred to as analytical enzymes).

At present, bovine serum albumin (BSA) is generally employed as a stabilizing agent for enzymes. BSA is a protein derived from bovine blood. In general, although not employed as a drug, a protein derived from animals must be handled with care in consideration of zoonosis (in the bovine, bovine spongiform encephalopathy (BSE), foot-mouth disease, or other diseases). BAS also has problems. For example, since the function of a certain enzyme is readily lost, even when BSA has been added, activity of the enzyme considerably decreases within a few days when the enzyme is maintained at room temperature in the form of solution. Therefore, there is keen demand for development of a stabilizing agent for enzymes which prevents deactivation and inactivation of enzymes, and which does not raise any problem of potential infection with a pathogen of BSE or other diseases.

SUMMARY OF THE INVENTION

The present inventors have carried out extensive studies in order to solve the aforementioned problems, and have found that a plant-derived polypeptide can remarkably enhance stability of enzymes, and that the polypeptide can be employed as a stabilizing agent for enzymes. The present invention has been accomplished on the basis of these findings.

Accordingly, in one aspect of the present invention, there is provided a stabilizing agent for an enzyme, the agent comprising a plant-derived polypeptide as an active ingredient.

Preferably, the plant-derived polypeptide is obtained by degradation of a plant-derived protein.

Preferably, the plant is an agricultural crop.

Preferably, the plant-derived polypeptide is obtained at least one plants selected from the group consisting of soybean, adzuki bean, kidney bean, broad bean, almond, peanut, wheat, corn, potato, and rice.

The protein may be at least one species selected from the group consisting of gliadin, zein, glutenin, gluten, hordein, oryzenin, glycinin, patatin, and conglycinin.

The enzyme is an analytical enzyme.

The analytical enzyme is for use in a clinical examination or immunoassay.

The enzyme for use in immunoassay is selected from the group consisting of peroxidase, alkaline phosphatase, β-galactosidase, acetylcholin esterase, and glucose oxidase.

The analytical enzyme is a complex with a substance of capable forming a specific binding pair (hereinafter referred to as specific-binding-pair-forming substance).

The analytical enzyme is a sugar-associated enzyme, a protein-associated enzyme, a lipid-associated enzyme, a nucleic-acid-associated enzyme, or a respiratory system-related enzyme.

In another aspect of the present invention, there is provided a stabilizing composition comprising the aforementioned stabilizing agent, and an alkali or a buffer.

The stabilizing composition may be in the form of sterilized solution through filtration, with a pH of 3.0 to 9.0.

In another aspect of the present invention, there is provided an enzyme composition comprising the stabilizing agent or the stabilizing composition, and an enzyme.

The composition may be in a dry state or in the solution form.

In another aspect of the present invention, there is provided a method for stabilizing an enzyme, the method comprising bringing a stabilizing agent or a stabilizing composition to coexist with the enzyme.

In another aspect of the present invention, there is provided a kit comprising the enzyme composition.

In another aspect of the present invention, there is provided use of a plant-derived polypeptide as a stabilizing agent for an enzyme.

DETAILED DESCRIPTION OF PREFERRED EMBODIMENTS

Best modes for carrying out the present invention will next be described.

The stabilizing agent of the present invention contains a plant-derived polypeptide as an active ingredient and is employed for stabilizing an enzyme.

In the present invention, the expression "stabilization of an enzyme" refers to stabilization of an enzyme during storage and against drying and/or heat. More specifically, the expression refers to a function for preventing deactivation or inactivation of the activity of an enzyme during long-term storage, drying, or freezing.

The term "plant" in relation to the stabilizing agent of the present invention refers to, for example, an agricultural product. Specific examples of preferred plants include wheat, barley, oat, corn, *Japonica* rice, *Indica* rice, *Javanica* rice, African rice, and glutinous rice, soybean, adzuki bean, kidney bean, broad bean, almond, peanut, potato, sweet potato, dasheen, and taro. Of these, soybean, wheat, corn, potato, and rice are more preferred, with soybean and corn being most preferred.

The "plant-derived polypeptide" contained in the stabilizing agent of the present invention is preferably a polypeptide which may be produced through degradation of the aforementioned plant-derived protein. The aforementioned plant-derived protein includes a protein extracted from a protein-containing portion of the above plant or a fraction containing the protein. Specific examples include reserve proteins such as gliadin, zein, glutenin, gluten, hordein, oryzenin, glycinin, patatin, and conglycinin; functional proteins such as lectin, amylase, and enzymes involved in respiration and photosynthesis; and structural proteins derived from roots, stalks, leaves, flowers, fruits, seeds, etc. Of these, reserve proteins are particularly preferred. In order to obtain the polypeptide from the protein, the protein may be degraded. No particular limitation is imposed on the method of degradation, so long as the method attains the object for obtaining polypeptide through reduction of molecular weight, and examples thereof include acid-hydrolysis, enzymatic hydrolysis, and alkali-hydrolysis.

Any enzyme can be employed for hydrolysis, so long as the enzyme belongs to the protease group and is able to degrade protein to form polypeptide. Examples of the enzyme include animal-derived proteases such as pepsin, trypsin, and chymotrypsin; plant-derived proteases such as papain, ficin, and bromelain; and other proteases derived from microorganisms such as bacteria, molds, and actinomycetes. Examples of the acid employed in acid-hydrolysis include hydrochloric acid, sulfuric acid, phosphoric acid, and nitric acid, and examples of the alkali substance employed in alkali-hydrolysis include sodium hydroxide, potassium hydroxide, and sodium carbonate. The polypeptide formed through hydrolysis preferably has a weight average molecular weight of 200 Da to 300,000 Da, more preferably 300 Da to 200,000 Da. Upon hydrolysis of protein, amino acid is formed. The stabilizing agent of the present invention may contain amino acid, so long as the agent contains polypeptide as an essential component.

Examples of preferred plant-derived polypeptides include a soybean protein hydrolyzate, a wheat protein hydrolyzate and derivatives thereof, a potato protein hydrolyzate, a corn protein hydrolyzate, and a rice bran protein hydrolyzate. Of these, a corn protein hydrolyzate is particularly preferred. Among corn protein hydrolyzates, a peptide having a molecular weight of 200 Da to 4,000 Da and a free amino acid content with respect to the total amino acid content of 1% or less is preferred. Moreover, a peptide having the following amino acid composition (wt. %) is more preferred: aspartic acid 2.5 to 12.5, threonine 2.5 to 6.0, serine 4.0 to 6.0, glutamic acid 15.0 to 50.0, glycine 2.0 to 5.5, alanine 2.0 to 13.5, valine 4.0 to 8.0, cysteine 0.0 to 1.5, methionine 1.0 to 2.0, isoleucine 3.0 to 6.0, leucine 6.0 to 15.0, tyrosine 1.0 to 4.0, phenylalanine 2.0 to 5.5, lysine 0.5 to 7.0, histidine 0.5 to 3.0, arginine 1.0 to 8.0, and proline 5.0 to 13.0.

Typical characteristics of each hydrolyzate are as follows:
<1> Soybean Protein Hydrolyzate
Appearance: pale yellow to brown
Total nitrogen content (%): 2.6 to 3.4
pH: 3.8 to 6.2
<2> Soybean Protein Peptone
<3> Soybean Protein Enzymatically Hydrolyzed Product
<4> Soybean Protein Acid-Hydrolyzed Product
<5> Wheat Protein Hydrolyzate
Appearance: brown liquid
Weight loss by drying (%): 75 to 80
Total nitrogen amount (%): 2.7 to 3.5
<6> Wheat Protein Hydrolyzate Derivative
Appearance: Grayish white
Total solid content (%): 81.3 to 100
Nitrogen (%): 13.0 to 16.0
Ashing residue (%): 13.5 or less
pH: 3.5 to 4.5
Water content (%): 5.0 or less
<7> Potato Protein Hydrolyzate
Appearance: yellow
Total solid content (%): 24.0 to 28.0
Nitrogen content (%): 2.5 to 4.0
Ashing residue (%): 4.5 or less
pH: 4.0 to 5.0
Molecular weight: 600
<8> Corn Protein Hydrolyzate
Appearance: White or pale yellow
Water content (%): 5.0 or less
Crude ash (%): 2.0 or less
Crude protein (%): 90.0 or more
Sugar content (%): 5.0 or less
Heavy metals (ppm): 4.0 or less
Arsenic (ppm): 1.0 or less
Molecular weight distribution: about 2 to 10 (oligopeptide)
Amino acid composition (wt. %): glutamic acid 24.67, leucine 13.69, alanine 12.99, proline 9.69, aspartic acid 6.04, serine 5.33, valine 4.94, threonine 3.95, isoleucine 3.77, tyrosine 3.42, glycine 2.39, phenylalanine 2.00, methionine 1.45, arginine 1.21, cysteine 1.07, lysine 1.00, and histidine 1.00.
<9> Rice Bran Protein Hydrolyzate
pH: 6.5 to 7.5
Molecular weight: 150,000

The target to be stabilized by the stabilizing agent of the present invention is an enzyme, and the origin, type, and form of its presence are not particularly limited. The enzyme is preferably an analytical enzyme. As used herein, the term "analytical enzyme" refers to an enzyme for use in analysis of pharmaceuticals, agricultural chemicals, foods, etc. No particular limitation is imposed on the analytical enzyme, so long as the enzyme is employed for an analytical purpose.

Examples of the analytical enzyme include an enzyme for use in clinical examinations, an enzyme for use in immunoassay, a sugar-associated enzyme, a protein-associated enzyme, a lipid-associated enzyme, a nucleic-acid-associated enzyme, and a respiratory system-related enzyme. Of these, enzymes for use in immunoassay are preferred.

Among analytical enzymes, the enzyme for use in clinical examination or the enzyme for use in immunoassay is an enzyme which is employed in clinical chemical analysis or in immunochemical analysis. No particular limitation is imposed on the type of enzyme, so long as the enzyme is employed in clinical examinations or immunoassay. Specific examples include peroxidase, alkaline phosphatase, β-galactosidase, acetylcholin esterase, glucose-6-phosphate dehydrogenase, alcohol oxidase, monoamine oxidase, lipase, amylase, protease, cellulase, catalase, acylase, glucose oxidase, cholesterol oxidase, cholesterol esterase, acyl-CoA oxidase, acyl-CoA synthetase, bilirubin oxidase, cholesterol dehydrogenase, glucose dehydrogenase, glycerol kinase, L-α-glycerophosphate oxidase, lactate dehydrogenase, lactate oxidase, lipoprotein lipase, malate dehydrogenase, and mutarotase. Among them, peroxidase, alkaline phosphatase, β-galactosidase, acetylcholin esterase, and glucose oxidase are preferred.

Examples of the sugar-associated enzyme include mannosidase, glucosidase, hyaluronidase, chondroitinase, heparitinase, and hyaluronan synthase. Examples of the protein-associated enzyme include pepsin, papain, proteinase, peptidase, and peptidyl transferase. Examples of the lipid-associated enzyme include lipase, phospholipase, and ceramidase. Examples of the nucleic-acid-associated enzyme include nuclease, DNA polymerase, restriction enzyme, and reverse transcriptase. Examples of the respiratory-system-related enzyme include glucokinase and glucose-6-phosphate dehydrogenase. Examples of other enzymes include phosphatase and sulfatase. Needless to say, the enzyme to be stabilized by the stabilizing agent of the present invention is not limited to the above-described enzymes.

The stabilizing agent of the present invention stabilizes an analytical enzyme or a complex of an analytical enzyme with a specific-binding-pair-forming substance. As used herein, the term "specific-binding-pair-forming substance" refers to one member of a pair of substances which form a binding pair through specific interaction (affinity) provided between biological substances. Specifically, the term refers to one substance of a pair such as an antibody and an antigen; biotin, and avidin or streptavidin; a specific sugar and the corresponding physiologically active substance such as lectin; cytokine, or chemokine, and the corresponding receptor; hyaluronic acid and a hyaluronic acid-binding substance; endotoxin and an endotoxin-neutralizing protein; or β-glucan and a β-glucan-binding protein.

The stabilizing agent composition of the present invention contains the aforementioned stabilizing agent, and an alkali or a buffer. Although the solution form thereof is particularly preferred, the composition may be in a dry state.

In other words, upon stabilization of an enzyme, the stabilizing agent of the present invention may be dissolved in an aqueous solvent containing an alkali, thereby providing a solution-form stabilizing agent. Examples of the alkali include alkali metal hydroxides and alkaline earth hydroxides. Of these, alkali metal hydroxides are particularly preferred. The alkali metal hydroxide is a hydroxide of an alkali metal such as potassium, lithium, or sodium and includes potassium hydroxide, lithium hydroxide, and sodium hydroxide. These alkali metal hydroxides may be used singly or in combination of two or more species, in the form of aqueous solution. Among the alkali metal hydroxides, sodium hydroxide is most preferred. The concentration of alkali metal hydroxide is generally 5 mmol/L to 2 mol/L, preferably 10 mmol/L to 500 mmol/L. The aforementioned aqueous solution generally has a pH of 3.0 to 9.0, preferably 6.5 to 8.0, more preferably 6.8 to 7.2.

In use, the stabilizing agent of the present invention may be dissolved in a buffer (buffer solution). Although no particular limitation is imposed on the type of the buffer, buffers such as a phosphate buffer, a Tris-HCl buffer, a Good's buffer, and a borate buffer are preferred. These buffers may be used singly or in combination of two or more species, and in an arbitrary amount.

Alternatively, the stabilizing agent of the present invention may be dissolved in an alkali metal hydroxide solution or a buffer so as to regulate the pH of the solution, and filtered for sterilization by means of a 0.22-μm filter or a similar filter, to thereby obtain a stabilizing agent composition employable in the present invention.

The stabilizing agent or the stabilizing agent composition of the present invention generally has a polypeptide concentration of 0.01 to 40% (w/v), preferably 0.1 to 30% (w/v).

The stabilizing agent or the stabilizing agent composition of the present invention stabilizes an enzyme, so as to maintain the activity thereof and to prevent deactivation. In a specific procedure, upon storage of an enzyme, the stabilizing agent or the stabilizing agent composition of the present invention is added to the enzyme so that the polypeptide concentration is adjusted to 0.01 to 10% (w/v), to thereby form an enzyme composition in the form of solution. The enzyme can be reliably stored in the composition solution or in a dried product of the enzyme composition solution. In actual use, the stabilizing agent or the stabilizing agent composition of the present invention may be added to a solution (e.g., phosphate buffered saline (PBS) solution) containing, for example, an enzyme in an amount of 1 pg/mL to 10 mg/mL.

In addition to the stabilizing agent or the stabilizing agent composition of the present invention and an enzyme, the aforementioned enzyme composition may further contain other stabilizing agents, a preservative, a surfactant, a sugar, or other peptide/proteins. The thus-prepared enzyme composition may be incorporated, as a component, into a kit employing an enzyme (e.g., an analytical kit). The enzyme composition is remarkably useful in that the quality of the kit can be maintained for a very prolonged period of time.

EXAMPLES

Example 1

Studies on Stabilizing Effect of the Stabilizing Agent of the Present Invention on an Enzyme-Labeled Antibody or on an Enzyme Methods <1> Preparation and Storage of a Horseradish Peroxidase (HRP)-Labeled Antibody Each of the test substances (stabilizing agents) listed in Tables 1 and 2 was dissolved in a 50 mmol/L Tris-HCl buffer (Tris-HCl: pH 7.3 to 7.7) containing 0.15 mol/L sodium chloride, 0.05% Tween 20, and 0.05% ProClin 300 (preservative) (hereinafter the buffer is referred to as T-TBS) so that a desired test substance concentration was attained. The mixture was filtered by means of a 0.22-μm filter, to thereby prepare a test substance solution. Horseradish peroxidase (HRP)-labeled goat anti-mouse IgG antibody (product of Jackson, hereinafter referred to as HRP-anti-mouse IgG antibody) was diluted 10,000 fold with the aforementioned test substance solution, and the diluted solution was tested. Stability of HRP-anti-mouse IgG antibody was investigated on the day of preparation (day 0), 5 days after storage at 37° C. (day 5), and 12 days after storage at 37° C. (day 12). Each test solution was cooled to room temperature before measurement of antibody activity. In Example 1, the following commercial products were employed: BSA (Seikagaku Corporation), gelatin and skim milk powder (Nacalai Tesque), and casein (Wako Pure Chemical Industries, Ltd.). Regarding the soybean protein hydrolyzed product, the wheat protein hydrolyzed product, the potato protein hydrolyzed product, and the corn protein hydrolyzed product, the aforementioned soybean protein peptone <2>, soybean protein enzymatically hydrolyzed product <3>, soybean protein acid-hydrolyzed product <4>, wheat protein hydrolyzate <5>, wheat protein hydrolyzate derivative <6>, potato protein hydrolyzate <7>, and corn protein hydrolyzate <8> were employed, respectively.

<2> Measurement of Activity of HRP-Labeled Antibody (i) Preparation of a Goat Anti-Mouse IgG Antibody Immobilized Plate A goat anti-mouse IgG antibody (product of Jackson) was diluted with phosphate buffered saline (pH 7.2 to 7.5, divalent-ion-free (e.g., Ca-ion-free); hereinafter referred to as PBS (−)) to 20 g/mL. The thus-prepared solution was added in an amount of 50 μL to each well of a Nunc-immuno plate (Product name; Maxi soap, product of Nunc) and stored at 4° C. for 14 to 18 hours, whereby the well was uniformly coated with the antibody. The plate was washed twice with PBS (−). In order to block a portion of the plate which had not been coated with the goat anti-mouse IgG antibody, PBS (−) solution containing 2% bovine serum albumin (BSA) (product of Seikagaku Corporation) serving as a blocking agent and 0.05% ProClin 300 serving as a preservative was added to each well of the plate, and the plate was left to stand at room temperature for two hours. Thereafter, the plate was washed four times with a washing solution (T-TBS), to thereby prepare a desired goat anti-mouse IgG antibody immobilized plate.

(ii) Measurement of Activity of an HRP-Labeled Antibody

After completion of washing, T-TBS containing 1% BSA (hereinafter referred to as reaction solution) (100 μL) was added to each well of a goat anti-mouse IgG antibody immobilized plate produced in the above-described (i). Subsequently, to each well, a mouse IgG having a concentration of 100 ng/mL controlled by the reaction solution or the reaction solution serving as a blank was added in an amount of 20 μL, and the mixture was allowed to stand at 37° C. for 60 minutes for performing antigen-antibody reaction.

After completion of the reaction, each well was washed four times with T-TBS. Subsequently, each HRP-anti-mouse IgG antibody solution (100 μL) containing a given test substance (stabilizing agent) prepared in the above-described (1) was added to each well, and the mixture was allowed to stand at 37° C. for 60 minutes for performing antibody-antigen-antibody reaction.

After completion of the reaction, the plate was washed four times with T-TBS. Subsequently, a tetramethylbenzidine (TMB) solution (100 μL) (product of Moss, inc.) serving as a substrate with respect to peroxidase was added to each well, and the mixture was allowed to react at 37° C. for 30 minutes for development. The developed reaction was terminated by adding 1N HCl (100 μL) to each well of the plate, and absorbance of the developed solution formed through degradation of TMB was measured at 450 nm (reference wavelength: 630 nm) by use of a well reader (SK-603, trade name, Seikagaku Corporation).

(iii) Measurement of Activity of HRP Contained in an HRP-Labeled Antibody

Each of the HRP-anti-mouse IgG antibody solutions containing a test substance prepared in (1) above was diluted 12 fold and added to each well in a volume of 10 μL. Subsequently, a tetramethylbenzidine (TMB) solution (100 μL) (product of Moss, inc.) serving as a substrate with respect to peroxidase was added to each well, and the mixture was allowed to react at 37° C. for 30 minutes for development. The developed reaction was terminated by adding 1N HCl (100 μL) to each well of the plate, and absorbance of the developed solution formed through degradation of TMB was measured at 450 nm (reference wavelength: 630 nm) by use of a well reader (SK-603, trade name, Seikagaku Corporation).

Reactivity of HRP-anti-mouse IgG in the presence of each test substance (stabilizing agent) was evaluated on the basis of difference in absorbance (i.e., between each sample reacted with mouse IgG (100 ng/mL) and the blank) (hereinafter referred to simply as absorbance difference). With respect to each test substance, stability of HRP-anti-mouse IgG in the presence of the test substance was represented by percent absorbance difference (residual activity; %); i.e., a ratio (×100) of absorbance difference of a sample at the corresponding test day to absorbance difference of the sample on the day of preparation of the sample (day 0). When a sample containing a test substance exhibited a residual activity not lower than −10 percent point of the residual activity of a control sample containing BSA, the test substance was evaluated to be acceptable(BB), whereas when the sample exhibited a residual activity equal to or higher than the residual activity of the control sample, the test substance was evaluated to have an excellent stabilizing effect(AA). Table 1 shows the stability of HRP-anti-mouse IgG antibody, and Table 2 shows the stability of HPR contained in HRP-anti-mouse IgG antibody.

TABLE 1

| | | Test substance | Concentration | Residual activity (%) day 0 | day 5 | day 12 | Rating |
|---|---|---|---|---|---|---|---|
| Control | | BSA | 1% | 100 | 73 | 68 | BB |
| | | Gelatin | 0.1% | 100 | 40 | 14 | DD |
| | | Casein | 0.1% | 100 | 83 | 69 | BB |
| | | Skim milk powder | 0.1% | 100 | 51 | 17 | DD |
| | | No additive | — | 100 | 24 | 4 | DD |
| Test group | Soybean protein | Peptone | 1% | 100 | 99 | 95 | AA |
| | | Enzymatically hydrolyzed product | 1% | 100 | 101 | 90 | AA |
| | | Acid-hydrolyzed product | 1% | 100 | 88 | 69 | BB |
| | Wheat protein (derivative) | Hydrolyzate | 1% | 100 | 78 | 74 | AA |
| | | Hydrolyzate derivative | 1% | 100 | 80 | 62 | BB |
| | Potato protein | Hydrolyzate | 1% | 100 | 91 | 78 | AA |
| | Corn protein | Enzymatically hydrolyzed product | 1% | 100 | — | 86 | AA |

Note:
Ratings for residual activity (day 12):
DD (0 to 30%),
CC (30 to 50%),
BB (50 to 70%), and
AA (≧70%)

TABLE 2

|  |  | Test substance | Concentration | Residual activity (%) day 0 | day 12 | Rating |
|---|---|---|---|---|---|---|
| Control |  | BSA | 1% | 100 | 64 | BB |
|  |  | No additive | 0% | 86 | 0 | DD |
| Test group | Soybean protein | Peptone | 1% | 88 | 83 | AA |
|  |  | Enzymatically hydrolyzed product | 1% | 85 | 84 | AA |
|  | Wheat protein | Hydrolyzate | 1% | 86 | 79 | AA |
|  | (derivative) | Hydrolyzate derivative | 1% | 86 | 87 | AA |
|  | Potato protein | Hydrolyzate | 1% | 89 | 76 | AA |
|  | Corn protein | Enzymatically hydrolyzed product | 1% | 87 | 84 | AA |

Note:
Ratings for residual activity are the same as defined in Table 1.

<3> Preparation and Storage of HRP

Each of the test substances (stabilizing agents) listed in Tables 3 and 4 was added to a 50 mmol/L Tris-HCl buffer (Tris-HCl: pH 7.3 to 7.7) containing 0.15 mol/L sodium chloride, 0.05% Tween 20, and 0.05% ProClin 300 (preservative) (hereinafter the buffer is referred to as T-TBS) so that a desired test substance concentration was attained. The mixture was filtered by means of a 0.22-μm filter, to thereby prepare a test substance solution. HRP (25 ng/mL) (hereinafter referred to as HRP (25)) having an activity equivalent to that of HRP contained in the HRP-anti-mouse IgG antibody employed in (1) above was diluted 10,000 fold with the aforementioned test substance solution, and the diluted solution was tested. In a similar manner, a solution of HRP (80 ng/mL) (hereinafter referred to as HRP (80)) having a concentration equivalent to that of IgG in relation to the HRP-anti-mouse IgG antibody was prepared and tested. Stability of HRP was investigated on the day of preparation (day 0) and 12 days after storage at 37° C. (day 12). Each test solution was cooled to room temperature before measurement of antibody activity. In this test, the aforementioned soybean protein hydrolyzate <1> was employed as the soybean protein (enzymatically hydrolyzed product).

<4> Measurement of HRP Activity

HRP (25) and HRP (80), prepared in (3) above, were diluted 12 fold and 20 fold, respectively. Each diluted solution was added to each well in a volume of 10 μL. Subsequently, a tetramethylbenzidine (TMB) solution (100 μL) (product of Moss, inc.) serving as a substrate with respect to peroxidase was added to each well, and the mixture was allowed to react at 37° C. for 30 minutes for development. The developed reaction was terminated by adding 1N HCl (100 μL) to each well of the plate, and absorbance of the developed solution formed through degradation of TMB was measured at 450 nm (reference wavelength: 630 nm) by use of a well reader (SK-603, trade name, Seikagaku Corporation).

Stability of HRP in the presence of each test substance (stabilizing agent) was represented by percent absorbance difference (residual activity; %); i.e., a ratio (×100) of absorbance difference of a sample at the corresponding test day to absorbance difference of the sample on the day of preparation of the sample (day 0). When a sample containing a test substance exhibited a residual activity not lower than −10 percent point of the residual activity of a control sample containing BSA, the test substance was evaluated to be acceptable (BB), whereas when the sample exhibited a residual activity equal to or higher than the residual activity of the control sample, the test substance was evaluated to have an excellent stabilizing effect (AA). Table 3 shows the stability of HRP (25), and Table 4 shows the stability of HPR (80).

TABLE 3

|  |  | Test substance | Concentration | Residual activity (%) day 0 | day 12 | Rating |
|---|---|---|---|---|---|---|
| Control |  | BSA | 1% | 100 | 49 | CC |
|  |  | No additive | 0% | 100 | 0 | DD |
| Test group | Soybean protein | Peptone | 1% | 101 | 73 | AA |
|  |  | Enzymatically hydrolyzed product | 1% | 99 | 73 | AA |
|  | Wheat protein | Hydrolyzate | 1% | 97 | 76 | AA |
|  | (derivative) | Hydrolyzate derivative | 1% | 98 | 68 | BB |
|  | Potato protein | Hydrolyzate | 1% | 98 | 70 | BB |
|  | Corn protein | Enzymatically hydrolyzed product | 1% | 100 | 84 | AA |

Note:
Ratings for residual activity are the same as defined in Table 1.

TABLE 4

|  | Test substance | Concentration | Residual activity (%) day 0 | Residual activity (%) day 12 | Rating |
|---|---|---|---|---|---|
| Control | BSA | 1% | 100 | 69 | BB |
|  | No additive | 0% | 94 | 0 | DD |
| Test group | Soybean protein Peptone | 1% | 100 | 84 | AA |
|  | Enzymatically hydrolyzed product | 1% | 93 | 85 | AA |
|  | Wheat protein Hydrolyzate | 1% | 99 | 90 | AA |
|  | (derivative) Hydrolyzate derivative | 1% | 97 | 85 | AA |
|  | Potato protein Hydrolyzate | 1% | 96 | 86 | AA |
|  | Corn protein Enzymatically hydrolyzed product | 1% | 95 | 100 | AA |

Note:
Ratings for residual activity are the same as defined in Table 1.

<5> Preparation and Storage of β-galactosidase

Each of the test substances (stabilizing agents) listed in Table 5 was diluted 2-fold with distilled water, and the mixture was filtered by means of a 0.22-μm filter, to thereby prepare a test substance solution. β-Galactosidase from sword-bean (product of Seikagaku Corporation, hereinafter referred to as GJ) was diluted with a 10 mM sodium phosphate buffer (pH: 7.2) so that the enzyme concentration was adjusted to 10 U/mL, and β-galactosidase from *E. Coli* (product of Sigma, hereinafter referred to as GE) was diluted with distilled water so that the enzyme concentration was adjusted to 64 U/mL. The above-diluted (2-fold) test substance solution was mixed with an equiamount of each of the above-prepared enzyme solutions, and the mixture was dispensed into vials, at a 40 μL aliquot per vial, followed by lyophilization. The thus-lyophilized enzyme product was tested. The enzyme activity of β-galactosidase was determined upon preparation, immediately after completion of lyophilization, and after storage for four weeks (4W) at 25° C., and obtained values were compared to evaluate stability. In this test, the soybean protein hydrolyzate <1> above was employed as the soybean protein (enzymatically hydrolyzed product), and the corn protein hydrolyzate <8> above was employed as the corn protein hydrolyzed product.

<6> Measurement of Activity of β-galactosidase

The enzyme activity of β-galactosidase was determined by use of p-nitrophenyl-β-galactoside serving as a substrate and evaluated on the basis of the absorbance of a sample. With respect to each test substance, enzyme stability was represented by percent absorbance (residual activity; %); i.e., a ratio (×100) of absorbance of a sample at each test time to absorbance of the sample upon preparation of the sample.

(i) Method for Measuring Enzyme Activity β-galactosidase from Sword-Bean

The enzyme and each test substance were diluted by use of a 10 mM sodium phosphate buffer (pH: 7.2) so that the enzyme concentration was adjusted to 0.83 U/mL, and the solution was employed as a test enzyme solution. A substrate solution was prepared by mixing a substrate with 100 mM phosphate-citrate buffer (pH 3.5) so that the concentration was adjusted to 1 mg/mL. Each test enzyme solution (10 μL) was added to the substrate solution (100 μL), and the mixture was allowed to react at 37° C. for 15 minutes. The enzymatic reaction was terminated by addition of a 1M sodium hydrogencarbonate (2 mL), and the absorbance of the resultant solution colored by the product was determined at 420 nm by a spectrophotometer. The test was run in triplicate. The results are shown in Table 5.

(ii) Method for Measuring Enzyme Activity of β-galactosidase from *E. coli*

The enzyme and each test substance were diluted by use of a 100 mM sodium phosphate buffer (pH: 7.2) containing 10 mM magnesium chloride so that the enzyme concentration was adjusted to 6.4 U/mL, and the solution was employed as a test enzyme solution. A substrate solution was prepared by mixing a substrate with distilled water so that the concentration was adjusted to 2 mg/mL. Each test enzyme solution (50 μL) was added to the substrate solution (50 μL), and the mixture was allowed to react at 37° C. for 15 minutes. The enzymatic reaction was terminated by addition of a 1M sodium hydrogencarbonate (2 mL), and the absorbance of the resultant solution colored by the product was determined at 420 nm by a spectrophotometer. The test was run in triplicate. The results are shown in Table 5.

TABLE 5

|  |  |  | Residual activity (%) |  |  |  |  |  |
|---|---|---|---|---|---|---|---|---|
|  |  |  | GJ | | | GE | | |
|  | Test substance | Concentration | After preparation | After lyophilization | 4W | After preparation | After lyophilization | 4W |
| Control group | No additive | 0% | 100 | 87 | 38 | 100 | 7 | 0 |
|  | BSA | 1% | 100 | 61 | 31 | 100 | 35 | 13 |
| Test group | Soybean protein hydrolyzate | 1% | 100 | 100 | 88 | 100 | 71 | 80 |
|  | Corn protein hydrolyzate | 1% | 100 | 107 | 106 | 100 | 74 | 75 |

<7> Preparation and Storage of α-mannosidase

Each of the test substances (stabilizing agents) listed in Table 6 was diluted 2-fold with distilled water, and the mixture was filtered by means of a 0.22-μm filter, to thereby prepare a test substance solution. α-Mannosidase from sword-bean (product of Seikagaku Corporation) was diluted with a 10 mmol/L sodium phosphate buffer (pH: 7.2) containing 1 mmol/L zinc chloride so that the enzyme concentration was adjusted to 228 U/mL. The above-diluted (2-fold) test substance solution was mixed with an equiamount of each of the above-prepared enzyme solutions, and the mixture was dispensed into vials, at a 40 μL aliquot per vial, followed by lyophilization. The thus-lyophilized enzyme product was tested. The enzyme activity of α-mannosidase was determined upon preparation, immediately after completion of lyophilization, and after storage for four weeks at 25° C., and the obtained values were compared to evaluate stability. In this test, the soybean protein hydrolyzate <1> above was employed as the soybean protein (enzymatically hydrolyzed product), and the corn protein hydrolyzate <8> above was employed as the corn protein hydrolyzed product.

<8> Method for Measuring Enzyme Activity of α-mannosidase

The enzyme activity of α-mannosidase was determined by use of p-nitrophenyl-α-mannoside serving as a substrate. The enzyme and each test substance were diluted by use of a 10 mmol/L sodium phosphate buffer (pH: 7.2) containing 1 mmol/L zinc chloride so that the enzyme concentration was adjusted to 1.14 U/mL, and the solution was employed as a test enzyme solution. A substrate solution was prepared by mixing a substrate with a 50 mmol/L phosphate-citrate buffer (pH: 4.5) so that the concentration was adjusted to 1 mg/mL. Each test enzyme solution (10 μL) was added to the substrate solution (100 μL), and the mixture was allowed to react at 37° C. for 15 minutes. The enzymatic reaction was terminated by addition of a 1M sodium hydrogencarbonate (2 mL), and the absorbance of the resultant solution colored by the product was determined at 420 nm by a spectrophotometer. The test was run in triplicate. The results are shown in Table 6. The enzyme activity was evaluated on the basis of the absorbance of a sample. With respect to each test substance, enzyme stability was represented by percent absorbance (residual activity; %); i.e., a ratio (×100) of absorbance of a sample at each test time to absorbance of the sample upon preparation of the sample. The results are shown in Table 6.

teins other than BSA, the residual activity was found to be 69% (casein), which is satisfactory, and 14% (gelatin) and 17% (skim milk powder), which are unsatisfactory.

In contrast, when the plant-derived substance (polypeptide) of the present invention is employed, remarkably excellent effect of stabilizing enzymes (residual activity: 60% or higher) was attained with respect to all plant-derived substances. Among them, the corn protein hydrolyzate and the soybean protein hydrolyzate attained remarkably high residual activity; i.e., 86% or higher and 90% or higher, respectively.

All the polypeptides of the present invention attained a remarkably excellent effect of stabilizing on HRP (25) and HRP (80); i.e., high residual activity of HRPs. Among them, the soybean protein hydrolyzate and the corn protein hydrolyzate attained remarkably high residual activity; i.e., 73% or higher and 84% or higher, respectively.

(II) Enzyme Activity of β-galactosidase

The residual activity of GJ after lyophilization was found to be 87% (without use of stabilizing agent) and 61% (with use of BSA), which were lower than the residual activity upon preparation thereof. However, when the soybean hydrolyzate or the corn hydrolyzate was present, the enzyme activity remained at 100 to 107%, which was approximately equal to the enzyme activity as measured immediately after preparation. The residual activity after storage at 25° C. for four weeks (4 W) was 38% (without use of stabilizing agent) and 31% (with use of BSA), which were further lower than the residual activity upon preparation thereof. However, when the soybean hydrolyzate or the corn hydrolyzate was present, the enzyme activity remained at 88 to 106%, indicating that the enzyme activity upon preparation was practically maintained. Thus, these hydrolyzate exhibited an excellent enzyme stabilizing effect as compared with BSA.

The residual activity of GE after lyophilization was found to be 7% (without use of stabilizing agent) and 35% (with use of BSA), which are considerably low. However, when the soybean hydrolyzate or the corn hydrolyzate was present, the residual activity was found to be 71 to 74%, which is higher than the enzyme activity obtained in the presence of BSA. The residual activity after storage at 25° C. for four weeks (4W) was considerably lowered to 0% (without use of stabilizing agent) and 13% (with use of BSA). However, when the soybean hydrolyzate or the corn hydrolyzate was present, the enzyme activity was found to be to 75 to 80%, indicating that

TABLE 6

|  | Test substance | Concentration | Residual activity (%) α-mannosidase | | |
| --- | --- | --- | --- | --- | --- |
|  |  |  | After preparation | After lyophilization | 4W |
| Control group | No additive | 0% | 100 | 12 | 0 |
|  | BSA | 1% | 100 | 44 | 21 |
| Test group | Soybean protein hydrolyzate | 1% | 100 | 101 | 81 |
|  | Corn protein hydrolyzate | 1% | 100 | 88 | 63 |

2. Results (I) Enzyme Activity of HRP

After storage at 37° C. for 12 days, residual activity of the HRP-anti-mouse IgG antibody was found to be 4% or less (without use of stabilizing agent) and 68% (in the presence of BSA). Regarding generally employed animal-derived prothe enzyme activity after lyophilization was practically maintained. Thus, these hydrolyzate exhibited an excellent enzyme stabilizing effect as compared with BSA.

(III) Enzyme Activity of α-mannosidase

The residual activity of α-mannosidase after lyophilization was considerably lowered to 12% (without use of stabilizing agent). When BAS was present, the residual activity was found to be 44%, which exhibited a higher stabilizing effect as compared with the case where no stabilizing agent was used, but which was lower than half the residual activity upon preparation thereof. In contrast, when any of the test substances of the test group (soybean hydrolyzate and corn hydrolyzate) was present, the enzyme activity remained at 88 to 101%, which was approximately equal to the enzyme activity upon preparation and indicated an excellent stabilizing effect as compared with BSA. The residual activity of α-mannosidase after storage at 25° C. for four weeks (4 W) was considerably lowered to 0% (without use of stabilizing agent) and 21% (with use of BSA). In contrast, when any of the test substances was present, the enzyme activity remained at 63 to 81%, which indicated a remarkably excellent stabilizing effect as compared with BSA. Particularly, when the soybean protein was present, the residual activity was found to be 81%, which was approximately equal to the enzyme activity upon preparation, indicating a remarkably excellent stabilizing effect.

The above results indicate that a hydrolyzed product of plant-derived protein exhibits an enzyme stabilizing effect higher than that of animal-derived protein.

As described above, the present invention provides a stabilizing agent for enzymes; a composition containing an enzyme and the stabilizing agent; and a kit containing the stabilizing agent. By bringing the stabilizing agent of the present invention to coexist with an enzyme, deactivation or inactivation of the activity of the enzyme during storage, drying, freezing, etc. can be prevented. The stabilizing agent does not raise any problem of potential infection of an enzyme with a pathogen.

What is claimed is:

1. A method for stabilizing an enzyme selected from the group consisting of peroxidase, alkaline phosphatase, β-galactosidase, acetylcholine esterase, and glucose oxidase, which is in a complex with at least one of the specific-binding-pair-forming substances selected from the group consisting of an antibody, an antigen, biotin, avidin, streptoavidin, lectin, cytokine, chemokine, and hyaluronic acid, endotoxin, β-glucan, to form an enzyme complex wherein the method comprises bringing a stabilizing agent into coexist with the enzyme complex and wherein the stabilizing agent comprises a hydrolyzate of plant-derived polypeptide as an active ingredient selected from the group consisting of a soybean protein hydrolyzate, a wheat protein hydrolyzate, a potato protein hydrolyzate, a corn protein hydrolyzate, and rice bran protein hydrolyzate, wherein said enzyme is stabilized.

2. The method according to claim 1, wherein the stabilizing agent is in a solution.

3. The method according to claim 2, wherein the solution additionally contains an alkali or buffer.

4. The method according to claim 2, wherein the solution is sterilized through filtration, with a pH of 3.0 to 9.0.

* * * * *